US008003084B2

(12) United States Patent
Gaudin

(10) Patent No.: US 8,003,084 B2
(45) Date of Patent: Aug. 23, 2011

(54) α-SUBSTITUTED CYCLOPENTANECARBONITRILES OR CYCLOHEXANECARBONITRILES AND THEIR USE IN PERFUMERY

(75) Inventor: Jean-Marc Gaudin, Annemasse (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 12/738,721

(22) PCT Filed: Nov. 4, 2008

(86) PCT No.: PCT/IB2008/054577
§ 371 (c)(1),
(2), (4) Date: Apr. 19, 2010

(87) PCT Pub. No.: WO2009/060378
PCT Pub. Date: May 14, 2009

(65) Prior Publication Data
US 2010/0247467 A1    Sep. 30, 2010

(30) Foreign Application Priority Data

Nov. 7, 2007 (WO) .................. PCT/IB2007/054516

(51) Int. Cl.
*A61Q 15/00* (2006.01)
*A61Q 13/00* (2006.01)
*A61L 9/01* (2006.01)
*C11D 3/50* (2006.01)
*A61K 8/40* (2006.01)

(52) U.S. Cl. ............ 424/65; 424/76.2; 510/106; 512/4; 512/6; 514/788

(58) Field of Classification Search .................. 424/65, 424/76.2; 510/106; 512/4, 6; 514/788; 558/432
See application file for complete search history.

(56) References Cited

U.S. PATENT DOCUMENTS 4,146,507 A    3/1979    DeSimone .................. 512/6

OTHER PUBLICATIONS

Aycard et al., "Interactions intramoleculaires. XIV. Interactions gauches avec un groupement *t*-butyle (series cyclohexanique et cyclohexénique)," Can. J. Chem., 51:741-747 (1973).
Cantrell, "Photochemical Reactions of α,β-Unsaturated Acids, Esters, and Nitriles," J. Org. Chem., 40(10):1447-1450 (1975).
Cormier et al., "Abstraction of Allylic Hydrogen vs. Other Processes in the Photochemistry of Three Doubly Unsaturated Ketones," Journal of the American Chemical Society, 96(6):1867-1873 (1974).
Dauben et al., "Light Induced Halogenative Decarboxylation of Thiohydroxamic Esters," Tetrahedron Letters, 30(19): 2461-2464 (1989).
Fleming et al., "Alkenenitriles: Zn-Cu Promoted Conjugate Additions of Alkyl Iodides in Water," Organic Letters, 8(8):1557-1559 (2006).
Fleming et al., "Alkenenitriles: Conjugate Additions of Alkyl Iodides with a Silica-Supported Zinc-Copper Matrix in Water," J. Org. Chem. 72:6961-6969 (2007).
Julia et al., "Cyclisation radicalaire. II. Cyclisation d'esters α-cyanés ε-éthyléniques en esters cyclohexaniques ou cyclopentaniques," Mémoire I, Bull. Soc. chim., 5:1109-1116 (1964).
Majetich et al., "A General Allylation Procedure Using Trimethylallylsilane and Fluoride Catalysis," J. Org. Chem., 51:1745-1753 (1986).
Majid et al., "Synthesis and Reactivity of Open-Chain and Cyclic 2-Cyano Zinc and Copper Organometallics," Tetrahedron Letters, 30(38): 5069-5072 (1989).
Zhang et al., "Carbon-Carbon Bond Formation via Opening of Epoxysilanes with Organometals Containing Lithium and Copper," J. Org. Chem., 54:2043-2044 (1989).
International Search Report and Written Opinion of the International Searching Authority, application No. PCT/IB2008/054577, Jun. 10, 2009.

*Primary Examiner* — Kamal Saeed
*Assistant Examiner* — Kristin Bianchi
(74) *Attorney, Agent, or Firm* — Winston & Strawn LLP

(57) ABSTRACT

The present invention relates to the field of perfumery. More particularly, it concerns α-substituted cyclopentanecarbonitriles or cyclohexanecarbonitriles. These compounds are valuable perfuming ingredients having fruity or jasminic odor notes. The present invention also concerns the compositions or articles containing the compound.

9 Claims, 1 Drawing Sheet

α-SUBSTITUTED CYCLOPENTANECARBONITRILES OR CYCLOHEXANECARBONITRILES AND THEIR USE IN PERFUMERY

This application is a 371 filing of International Patent Application PCT/IB2008/054577, filed Nov. 4, 2008.

TECHNICAL FIELD

The present invention relates to the field of perfumery. More particularly, it concerns α-substituted cyclopentanecarbonitriles or cyclohexanecarbonitriles. Said compounds are valuable perfuming ingredients having fruity and/or jasminic odor notes. The present invention also concerns the compositions or articles containing said compounds.

PRIOR ART

To the best of our knowledge, none of the present cyclopentane or cyclopentene compounds are known in the prior art. Some cyclohexanecarbonitrile derivatives are known in the literature. Indeed, 2-(5-hexenyl)-cyclohexanecarbonitrile (Organic Letters (2006), 8(8), 1557-1559), 2-(4-methyl-3-pentenyl)-cyclohexanecarbonitrile, 2-(4-methyl-3-pentenyl)-cyclohexanecarbonitrile and 2-(2-methyl-2-propenyl)-cylohexanecarbonitrile (Tetrahedron Letters (1978), 28, 2461-2464), 2-(1,2-dimethyl-2-propenyl)-cyclohexanecarbonitrile (Journal of Organic Chemistry (1975), 40(10), 1447-1450) and 2-(1,1-dimethylethyl)-cyclohexanecarbonitrile (Canadian Journal of Chemistry (1973), 51(5), 741-747) are known. However, these prior art documents do not report or suggest any organoleptic properties of these compounds or of the compounds of the invention. They also do not report or suggest any use of said compounds in the field of perfumery.

The closest structural analogue known from the prior art as perfuming ingredient is in fact quite different structurally, since it is a kotone. Said compound is 2-heptylcyclopentanone, disclosed together with their organoleptic properties in S. Arctander, Perfume and Flavor Chemicals, 1969, Montclair, N.J., USA, N° 1534. However, these compounds can not be perceived by the person skilled in the art as anticipating the compound of the present invention and their uses, since they don't have the same number of carbon atoms and since they bear a different functional group.

DESCRIPTION OF THE INVENTION

We have now surprisingly discovered that a compound of formula (I),

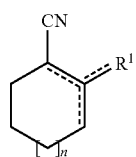

(I)

wherein one dotted line represents a single or a double bond and two dotted lines represent single bonds, n is 0 or 1, $R^1$ is a $C_3$ to $C_8$ alkyl or alkenyl group, and said compound is in the form of any of its diastereoisomers or of a mixture thereof;

can be advantageously used as perfuming ingredients, for instance to impart odor notes of the jasminic, fruity (e.g. apricot), lactonic and/or celery type.

For the sake of clarity, by the expression "wherein one dotted line represents a single or a double bond and two dotted lines represent single bonds", or the similar, it is meant the normal meaning understood by a person skilled in the art, i.e. that the whole bonding (solid and dotted line) between the carbon atoms connected by said dotted line is a carbon-carbon single or a carbon-carbon double bond.

According to another embodiment of the invention, there can be used as perfuming ingredient a compound of formula

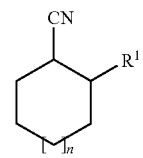

(II)

wherein n is 0 or 1, $R^1$ is a $C_3$ to $C_8$ alkyl or alkenyl group, and said compound is in the form of any of its diastereoisomers or of a mixture thereof.

According to any one of the above embodiment of the invention, said compounds of formula (I) or (II) are those wherein $R^1$ is a $C_4$ to $C_8$, or a $C_5$ to $C_7$, alkyl group.

According to another embodiment of the invention, there can be used as perfuming ingredient a compound of formula (I), wherein $R^1$ is a linear alkyl or alkenyl group.

According to any one of the above embodiment of the invention, said compounds of formula (I) or (II) are those wherein n is 0.

According to a further embodiment of the invention, said compound (II) is a compound of formula (III) or (IV)

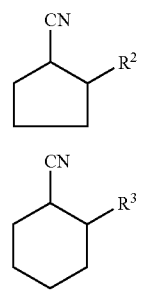

(III)

(IV)

wherein $R^2$ represents a $C_{5-8}$ linear or cyclic alkyl or alkenyl group, and $R^3$ represents a $C_{3-6}$ linear or cyclic alkyl or alkenyl group.

Yet, according to a particular embodiment of the invention, there can be used as perfuming ingredient 2-[(2E)-2-octenyl]cyclopentanecarbonitrile, 1,1'-bi(cyclopentyl-2-carbonitrile, 1,1'-bi(cyclohexyl)-2-carbonitrile, 2-propylcyclohexanecarbonitrile, 2-allylcyclohexanecarbonitrile, 2-heptylcyclopentanecarbonitrile or 2-pentylcyclopentanecarbonitrile, in the form of any of its diastereoisomers or of a mixture thereof. 2-Heptylcyclopentanecarbonitrile or 2-pentylcyclopentanecarbonitrile represents a particularly appreciated embodiment of the invention.

The compounds of formula (I), as well as (II), (III) or (IV) are novel compounds, and therefore are an object of the present invention, at the exception 2-(5-hexenyl)-cyclohexanecarbonitrile, 2-(4-methyl-3-pentenyl)-cyclohexanecarbonitrile, 2-(4-methyl-3-pentenyl)-cyclohexanecarbonitrile, 2-(2-methyl-2-propenyl)-cylohexanecarbonitrile, 2-(1,2-dimethyl-2-propenyl)-cylohexanecarbonitrile and 2-(1,1-dimethylethyl)-cyclohexanecarbonitrile, as mentioned above.

According to an embodiment of the invention, said novel compound are those of formula (I) or (II) wherein
n is 1 and $R^1$ is a $C_4$ to $C_8$ alkyl group except $^tBu$; or
n is 0 and $R^1$ is a $C_4$ to $C_8$ alkyl or alkenyl group.

As mentioned above, the general odor type of the invention's compound of formula (I) comprises jasminic, fruity (e.g. apricot), lactonic and/or celery notes type. In particular, those of formula (III) comprise jasminic, apricot and/or lactonic notes and those of formula (IV) comprise celery and/or floral (e.g. jasminic or rosy) notes.

As a typical example of the invention's compounds, one my cite 2-heptylcyclopentanecarbonitrile. The odor of this compound can be described as having a fruity-apricot peal, lactonic, jasminic odor note, with a coriander leaves aspect. In fact the overall odor impression of said compound is almost lactonic, which is totally unexpected for a nitrile derivative. From a perfumery point of view, and despite the important structural differences, the invention nitrile is to be compared with known perfumery lactones such as δ-undecalactone and γ-decalactone. However the invention nitrile still distinguishes from said lactones by imparting more natural, velvety notes, altogether with jasminic and coriander notes, providing thus an original combination of characters. Furthermore, the present nitrile shows an excellent substantivity and a better stability than the cited lactones in several difficult applications, which is always an advantage.

When 2-heptylcyclopentanecarbonitrile is compared to the much heavier and substituted Veloutone (2,2,5-trimethyl-5-pentyl-1-cyclopentanone; origin: Firmenich SA) known and widely used to confer jasminic, lactonic and fruity notes, then the invention's compound possesses a more lactonic and less fruity-velvety character.

As other typical example of the invention, one may cite also 2-pentylcyclopentanecarbonitrile. The odor of this compound can also be described as having floral-jasminic with spicy-celery side notes together with a well perceivable lactonic connotation.

As other typical examples of the invention, one may cite also: 2-[(2E)-2-octenyl]cyclopentanecarbonitrile, odor: apricot, lactonic aspect; 1,1'-bi(cyclopentyl)-2-carbonitrile, odor: floral jasminic, celery, lactonic notes; 2-propylcyclohexanecarbonitrile, odor: floral jasminic, celery, lactonic, minty notes; 1,1'-bi(cyclohexyl)-2-carbonitrile, odor: rosy, phenylethylol, cinnamic, celery notes.

Now, as mentioned above, the closest structural analogues of the present nitriles known in the prior art as perfuming ingredients are pretty different in structure and organoleptic character.

When the present invention nitrile is compared to the prior art, the present invention compounds distinguish themselves by lacking of, or by not possessing significant, green/herbaceous odor notes, and by having a lactonic and/or celery character.

In particular, when the odor of 2-heptylcyclopentanecarbonitrile is compared with 2-heptylcyclopentanone, then the invention compound distinguishes itself by having lactonic, apricot-peach and coconut odor notes (absent in 2-heptylcyclopentanone), and by lacking of green-herbaceous/acidic odor notes characteristic of 2-heptylcyclopentanone.

Said differences lend the invention's compounds and the prior art compounds to be each suitable for different uses, i.e. to impart different organoleptic impressions.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one compound of formula (I), as described in any of the above embodiments;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs—und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the compounds of formula (I) that can be used as perfuming ingredients or the compositions, as disclosed in any of the above embodiments, can be advantageously used in all the fields of modern perfumery to positively impart or modify the odor of a consumer product into which said compound (I) is added. Consequently, a perfumed article comprising:
i) as perfuming ingredient, at least one compound of formula (I), as defined above; and
ii) a consumer product base;
is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 10% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

EXAMPLES

Figure 1:
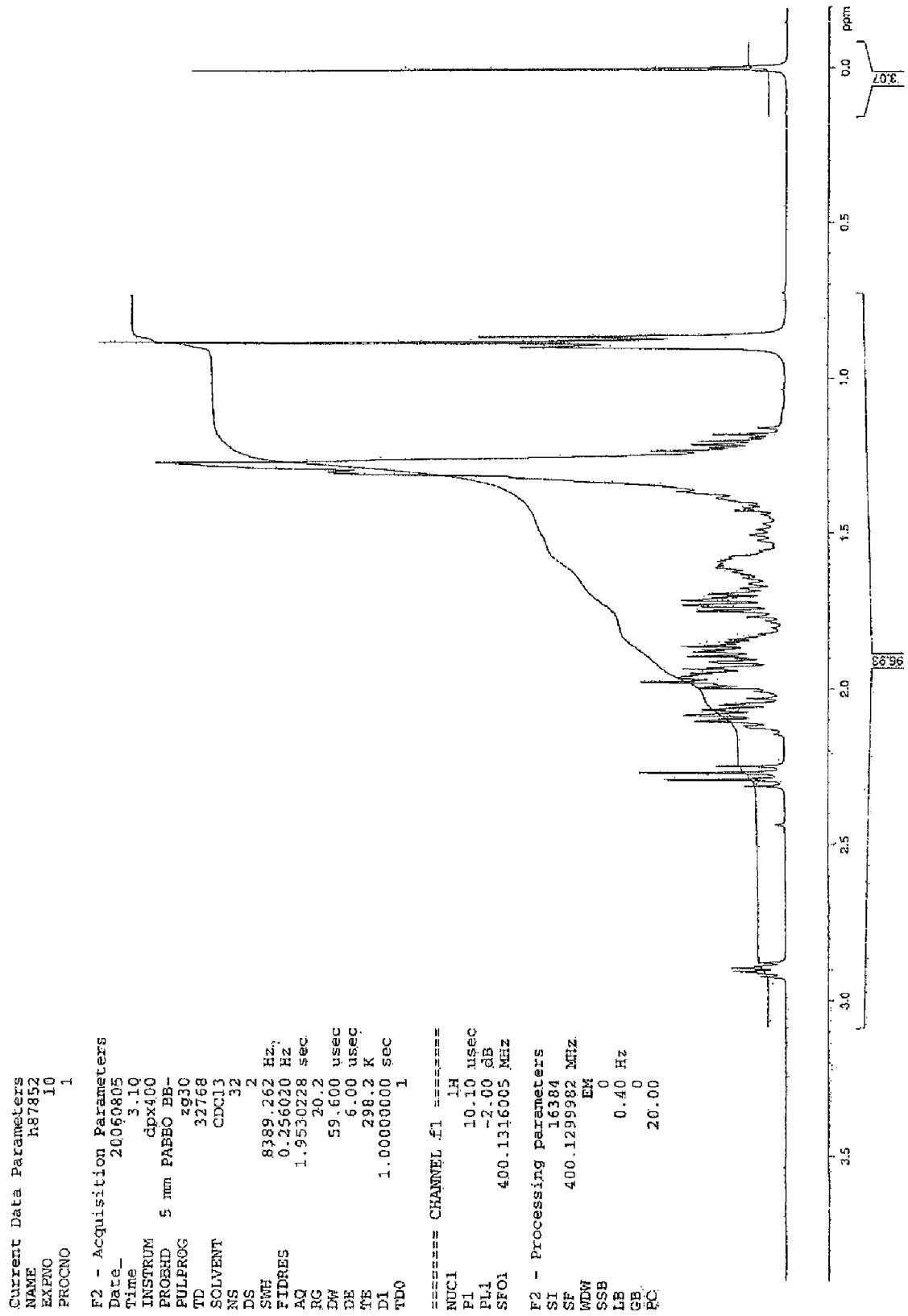
FIG. 1 represents the $^1$H-NMR spectrum of 2-heptylcyclopentanecarbonitrile, as prepared by the method of example 1.

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical displacements δ are indicated in ppm with respect to TMS as standard, the coupling constants J are expressed in Hz.

Example 1

Synthesis of Compounds of Formula (I)

Synthesis of 2-heptylcyclopentanecarbonitrile 27.6 g of tosylmethyl isocyanide and 20 g of 2-heptylcyclopentanone were dissolved in 400 ml of 1,2-dimethoxyethane and 10 ml of ethanol. The solution was cooled to 0° C. with an ice-bath, and 29 g of $^t$BuOK were added in 1 hour maintaining the temperature between 0 and 10° C. After completion of the reaction, the reaction mixture was poured into water and extracted with cyclohexane. The organic layer was washed 3 times with water until neutral pH. Purification by bulb-to-bulb distillation (150° C./0.06 mbar) gave 13.4 g of the pure 2-heptylcyclopentanecarbonitrile.

$^{13}$C-NMR: 14.10 (q); 22.68 (t); 23.18 (t); 24.21 (t); 28.09 (t); 28.53 (t); 29.22 (t); 29.25 (t); 29.67 (t); 30.55 (t); 30.60 (t); 30.81 (t); 31.83 (t); 31.85 (t); 31.87 (t); 32.17 (t); 33.95 (d); 34.40 (d); 34.70 (t); 43.00 (d); 45.94 (d); 121.45 (s); 123.26 (s).

IR: 2955, 2924, 2855, 2235, 1626, 1455, 1377, 1304, 1125, 911, 889, 723 cm$^{-1}$.

Synthesis of 2-pentylcyclopentanecarbonitrile 27.6 g of tosylmethyl isocyanide and 17 g of 2-pentylcyclopentanone were dissolved in 400 ml of 1,2-dimethoxyethane and 10 ml of ethanol. The solution was cooled to 0° C. with an ice-bath, and 29 g of $^t$BuOK were added in 1 hour maintaining the temperature between 0 and 10° C. After completion of the reaction, the reaction mixture was poured into water and extracted with cyclohexane. The organic layer was washed 3 times with water until neutral pH. Purification by bulb-to-bulb distillation (130° C./0.06 mbar) gave 10.7 g of the pure 2-pentylcyclopentanecarbonitrile.

$^{13}$C-NMR: 14.04 (q); 22.56 (t); 22.58 (t); 23.17 (t); 24.21 (t); 27.74 (t); 28.17 (t); 30.54 (t); 30.60 (t); 30.80 (t); 31.82 (t); 31.88 (t); 32.11 (t); 33.93 (d); 34.40 (d); 34.64 (t); 43.00 (d); 45.93 (d); 121.48 (s); 123.29 (s).

Using the same experimental procedure as the two examples above (same molar amounts and work up), the following compounds were also obtained:

2-[(2E)-2-octenyl]cyclopentanecarbonitrile

From 2-[(2E)-2-octenyl]cyclopentanone in 48% yield after flash chromatographic purification (cis/trans ratio 50/50)

$^{13}$C-NMR: 14.07 (q), 22.53 (t), 23.08 (t), 24.21 (t), 29.13 (t), 29.17 (t), 30.19 (t), 30.46 (t), 30.77 (t), 31.19 (t), 31.40 (t), 31.41 (t), 32.52 (t), 32.55 (t), 33.39 (d), 33.74 (d), 35.16 (t), 37.11 (t), 43.22 (d), 45.66 (d), 121.32 (s), 123.08 (s), 126.72 (d), 127.50 (d), 132.85 (d), 133.49 (d)

1,1'-bi(cyclopentyl)-2-carbonitrile

From 2-(cyclopentyl)-cyclopentanone with 60% yield after flash chromatographic purification (cis/trans ratio 50/50)

$^{13}$C-NMR: 23.17 (t), 24.73 (t), 25.01 (t), 25.21 (t), 25.24 (t), 25.40 (t), 30.02 (t), 30.72 (t), 31.15 (t), 31.19 (t), 31.39 (t), 31.55 (t), 32.06 (t), 32.14 (t), 32.21 (d), 33.99 (d), 43.19 (d), 45.42 (d), 50.03 (d), 50.98 (d), 121.71 (s), 123.79 (s)

2-allylcyclohexanecarbonitrile

From 2-allylcyclohexanone with 60% yield after flash chromatographic purification (cis/trans ratio 50/50)

$^{13}$C-NMR: 22.25 (t), 24.88 (t), 24.91 (t), 25.36 (t), 28.89 (t), 28.97 (t), 29.93 (t), 30.25 (t), 32.39 (d), 33.92 (d), 38.62 (d), 38.75 (t), 39.13 (t), 39.56 (d), 117.34 (t), 117.66 (t), 120.39 (s), 122.08 (s), 134.71 (d), 135.30 (d);

2-propylcyclohexanecarbonitrile

From 2-propylcyclohexanone with 60% yield after flash chromatographic purification (cis/trans ratio 50/50

$^{13}$C-NMR: 14.07 (q), 14.15 (q), 19.40 (t), 19.75 (t), 22.40 (t), 24.98 (t), 25.05 (t), 25.38 (t), 29.01 (t), 29.05 (t), 30.16 (t), 30.54 (t), 32.92 (d), 34.97 (d), 36.86 (t), 36.92 (t), 38.48 (d), 39.63 (d), 120.69 (s), 122.44 (s)

1,1'-bi(cyclohexyl)-2-carbonitrile

From 2-(cyclohexyl)-cyclohexanone with 20% yield after flash chromatographic purification (cis/trans ratio 50/50)

$^{13}$C-NMR: 22.29 (t), 25.26 (t), 25.35 (t), 25.82 (t), 26.15 (t), 26.19 (t), 26.41 (t), 26.43 (t), 26.59 (t), 26.64 (t), 26.77 (t), 26.97 (t), 29.45 (t), 30.36 (t), 30.53 (t), 30.63 (t), 31.34 (t), 32.17 (d), 40.27 (d), 40.44 (d), 44.51 (d), 45.31 (d), 120.99 (s), 122.32 (s);

Example 2

Preparation of a Perfuming Composition

A floral-fruity perfume was prepared by admixing the following ingredients:

| Ingredient | Parts by weight |
| --- | --- |
| 1,1-Dimethyl-2-phenylethyl acetate | 20 |
| Phenylethyl Acetate | 25 |
| 10%* 4-(4-Hydroxy-1-phenyl)-2-butanone | 10 |
| 10%* Cetalox ®[1)] | 20 |
| Coumarine | 20 |
| Dihydroeugenol | 5 |
| Dimethyloctanol | 30 |
| Exaltolide Total ®[2)] | 100 |
| Diethyl 1,4-cyclohexane dicarboxylate[3)] | 15 |
| Iralia Total ®[4)] | 60 |
| Hedione ®[5)] | 80 |
| Lilial ®[6)] | 25 |
| Lorysia ®[7)] | 85 |
| Phenylhexanol | 140 |
| Benzyl salicylate | 60 |
| Linalool | 110 |
| Verdox ®[8)] | 30 |
| Vertofix ®[9)] | 80 |
| Tamarin Base 41310 G[10)] | 35 |
| | 950 |

*in dipropyleneglycol
[1)]dodecahydro-3a,6,6,9a-tetramethyl-naphtho[2,1-b]furan; origin: Firmenich SA, Geneva, Switzerland
[2)]pentadecanolide; origin: Firmenich SA, Geneva, Switzerland
[3)]origin: Firmenich SA, Geneva, Switzerland
[4)]isomers mixture of methylionones, origin: Firmenich SA, Geneva, Switzerland
[5)]methyl dihydrojasmonate, origin: Firmenich SA, Geneva, Switzerland
[6)]3-(4-tert-butylphenyl)-2-methylpropanal, origin: Givaudan-Roure SA, Vernier, Switzerland
[7)]4-(1,1-demethylethyl)-1-cyclochexyl acetate, origin Firmenich SA, Geneva, Switzerland
[8)]2-tert-butyl-1-cyclohexyl acetate, origin: International Flavors & Fragrances, USA
[9)]methyl cedryl ketone, origin: International Flavors & Fragrances, USA
[10)]compounded perfumery base, origin: Firmenich SA, Geneva, Switzerland The addition of 50 parts by weight of 2-heptylcyclopentanecarbonitrile to the above-described accord imparted to the fragrance of the latter a nice apricot, lactonic and slightly floral-jasmine note.

When, instead of the invention's compound, there was added the same amount of lactones, it was obtained a perfume having an alimentary aspect, which does not suit with the desired accord.

When, instead of the invention's compound, there was added the same amount of 2-heptylcyclopentanone, it was obtained a more aggressive perfume, due to the presence of unsuitable green notes, as well as to weaker fruity and lack of lactonic notes.

Example 3

Preparation of a Perfuming Composition

A fruity-jasmine accord was prepared by admixing the following ingredients:

| Ingredient | Parts by weight |
| --- | --- |
| Benzyl Acetate | 100 |
| 4-Cyclohexyl-2-methyl-2-butanol[1)] | 50 |
| Coumarine | 15 |
| Exaltolide Total ®[2)] | 100 |
| Florol ®[3)] | 100 |

-continued

| Ingredient | Parts by weight |
|---|---|
| Hedione ®[4] | 240 |
| Linalool | 240 |
| Orange essential oil | 100 |
| 10%* Vanillin | 10 |
| Passion fruit Base 109223[5] | 15 |
| | 970 |

*in dipropyleneglycol
[1] origin: Firmenich SA, Geneva, Switzerland
[2] pentadecanolide; origin: Firmenich SA, Geneva, Switzerland
[3] tetrahydro-2-isobutyl-4-methyl-4(2H)-pyranol; origin: Firmenich SA, Geneva, Switzerland
[4] methyl deihydrojasmonate, origin: Firmenich SA, Geneva, Switzerland
[5] compounded perfumery base; origin: Firmenich SA, Geneva, Switzerland The addition of 30 parts by weight of 2-heptylcyclopentanecarbonitrile to the above-described simple fruity-jasmine accord strengthens the fruity aspect and sweetness by imparting a very natural apricot peal note.

When, instead of the invention's compound, there was added the same amount of 2-heptylcyclopentanone, it was obtained a perfume more aggressive due to the presence of unsuitable green notes, as well as to weaker fruity and lack of lactonic notes.

Example 4

Preparation of a Perfuming Composition

A floral-jasmine accord was prepared by admixing the following ingredients:

| Ingredient | Parts by weight |
|---|---|
| Benzyl Acetate | 50 |
| Hexylcinnamic aldehyde | 200 |
| 2-Methylundecanal | 5 |
| Methyl anthranilate | 25 |
| Benzylacetone | 25 |
| Citronellyl Nitrile | 5 |
| 4-Cyclohexyl-2-methyl-2-butanol[1] | 100 |
| 10%* Allyl Cyclohexylpropionate | 5 |
| 10%* α-Damascone | 15 |
| Iralia Total ®[2] | 60 |
| Hedione ®[3] | 40 |
| Habanolide ®[4] | 50 |
| Linalool | 200 |
| Mayol ®[5] | 50 |
| Phenethylol | 130 |
| Verdyl propionate | 10 |
| | 970 |

*in dipropyleneglycol
[1] origin: Firmenich SA, Geneva, Switzerland
[2] isomers mixture of methylionones, origin: Firmenich SA, Geneva, Switzerland
[3] methyl dihydrojasmonate, origin: Firmenich SA, Geneva, Switzerland
[4] pentadecenolide; origin: Firmenich SA, Geneva, Switzerland
[5] cis-7-P-menthanol The addition of 30 parts by weight of 2-heptylcyclopentanecarbonitrile to the above-described accord strengthened the jasmine note while rendering it sweeter and more natural, and prolonged this effect all long the evaporation.

When, instead of the invention's compound, there was added the same amount of 2-heptylcyclopentanone, it was obtained a perfume more aggressive due to the presence of unsuitable green notes, as well as to weaker fruity and lack of lactonic notes.

What is claimed is:

1. A perfuming composition comprising:
    i) as perfuming ingredient, at least one compound of formula (II)

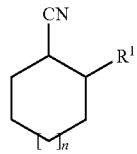

(II)

wherein n is 0 or 1, $R^1$ is a $C_3$ to $C_8$ alkyl or alkenyl group, and the compound is in the form of any of its diastereoisomers or of a mixture thereof;
    ii) at least one ingredient selected from the group consisting of a perfumery carrier and a perfumery base; and
    iii) optionally at least one perfumery adjuvant.

2. A perfumed article comprising:
    i) as perfuming ingredient, at least one compound of formula (II)

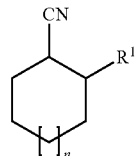

(II)

wherein n is 0 or 1, $R^1$ is a $C_3$ to $C_8$ alkyl or alkenyl group, and the compound is in the form of any of its diastereoisomers or of a mixture thereof; and
    ii) a consumer product base.

3. The perfumed article according to claim 2, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

4. A method to confer, enhance, improve or modify the odor properties of a perfuming composition or of a perfumed article, which method comprises adding to the composition or article an effective amount of at least a compound of formula (II)

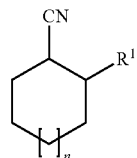

(II)

wherein n is 0 or 1, $R^1$ is a $C_3$ to $C_8$ alkyl or alkenyl group, and the compound is in the form of any of its diastereoisomers or of a mixture thereof.

5. The method of claim 4, wherein $R^1$ is a $C_4$ to $C_8$ alkyl group.

6. The method of claim 4, wherein n is 0.

7. The method of claim 4, wherein the compound of formula (I) is 2-heptylcyclopentanecarbonitrile or 2-pentylcyclopentanecarbonitrile, in the form of any of its diastereoisomers or of a mixture thereof.

8. The perfuming composition of claim 1, wherein the compound of formula (I) is 2-heptylcyclopentanecarbonitrile or 2-pentylcyclopentanecarbonitrile, in the form of any of its diastereoisomers or of a mixture thereof.

9. The perfumed article of claim 2, wherein the compound of formula (I) is 2-heptylcyclopentanecarbonitrile or 2-pentylcyclopentanecarbonitrile, in the form of any of its diastereoisomers or of a mixture thereof.

* * * * *